United States Patent
Trudel

(10) Patent No.: US 8,377,365 B2
(45) Date of Patent: Feb. 19, 2013

(54) SYSTEM AND METHOD FOR STENT MANUFACTURE

(75) Inventor: Julie Trudel, Santa Rosa, CA (US)

(73) Assignee: Medtronic Vascular, Inc., Santa Rosa, CA (US)

( * ) Notice: Subject to any disclaimer, the term of this patent is extended or adjusted under 35 U.S.C. 154(b) by 345 days.

(21) Appl. No.: 12/769,785

(22) Filed: Apr. 29, 2010

(65) Prior Publication Data

US 2011/0266720 A1   Nov. 3, 2011

(51) Int. Cl.
*B29C 41/00* (2006.01)
(52) U.S. Cl. .................. 264/484; 264/460; 264/405
(58) Field of Classification Search .............. 264/405, 264/460, 484
See application file for complete search history.

(56) References Cited

U.S. PATENT DOCUMENTS

| | | | |
|---|---|---|---|
| 4,323,525 A * | 4/1982 | Bornat | 264/441 |
| 4,739,762 A | 4/1988 | Palmaz | |
| 5,133,732 A | 7/1992 | Wiktor | |
| 5,292,331 A | 3/1994 | Boneau | |
| 5,421,955 A | 6/1995 | Lau et al. | |
| 5,605,696 A | 2/1997 | Eury et al. | |
| 6,090,127 A | 7/2000 | Globerman | |
| 6,165,212 A * | 12/2000 | Dereume et al. | 623/1.13 |
| 2005/0064168 A1 * | 3/2005 | Dvorsky et al. | 428/292.1 |
| 2009/0142505 A1 * | 6/2009 | Orr et al. | 427/458 |

FOREIGN PATENT DOCUMENTS

| WO | WO 2008/086369 | 7/2008 |
|---|---|---|
| WO | WO 2008/148013 | 12/2008 |

* cited by examiner

*Primary Examiner* — Galen Hauth

(57) ABSTRACT

The system and method for stent manufacture includes a method of supercritical stent manufacture including mixing a polymer and a supercritical fluid to form a supercritical mixture; electrically charging a mold to a first polarity, the mold having a mold wall defining a mold plenum; discharging the supercritical mixture through a nozzle; electrically charging the supercritical mixture to a second polarity opposite the first polarity; repeatedly directing the charged supercritical mixture into the mold plenum to form a plurality of polymer layers on the mold wall, the plurality of polymer layers having a predetermined thickness; and separating the plurality of polymer layers from the mold wall.

17 Claims, 5 Drawing Sheets

SYSTEM AND METHOD FOR STENT MANUFACTURE

TECHNICAL FIELD

The technical field of this disclosure is systems and methods of manufacturing medical implant devices, particularly, systems and methods of manufacturing stents.

BACKGROUND OF THE INVENTION

Stents are generally cylindrical shaped devices that are radially expandable to hold open a segment of a blood vessel or other anatomical lumen after implantation into the body lumen. Stents have been developed with coatings to deliver drugs or other therapeutic agents.

Stents are used in conjunction with balloon catheters in a variety of medical therapeutic applications including intravascular angioplasty. For example, a balloon catheter device is inflated during PTCA (percutaneous transluminal coronary angioplasty) to dilate a stenotic blood vessel. The stenosis may be the result of a lesion such as a plaque or thrombus. After inflation, the pressurized balloon exerts a compressive force on the lesion thereby increasing the inner diameter of the affected vessel. The increased interior vessel diameter facilitates improved blood flow. Soon after the procedure, however, a significant proportion of treated vessels re-narrow.

To prevent restenosis, short flexible cylinders, or stents, constructed of metal or various polymers are implanted within the vessel to maintain lumen size. The stents acts as a scaffold to support the lumen in an open position. Various configurations of stents include a cylindrical tube defined by a mesh, interconnected stents or like segments. Some exemplary stents are disclosed in U.S. Pat. No. 5,292,331 to Boneau, U.S. Pat. No. 6,090,127 to Globerman, U.S. Pat. No. 5,133,732 to Wiktor, U.S. Pat. No. 4,739,762 to Palmaz and U.S. Pat. No. 5,421,955 to Lau. Balloon-expandable stents are mounted on a collapsed balloon at a diameter smaller than when the stents are deployed. Stents can also be self-expanding, growing to a final diameter when deployed without mechanical assistance from a balloon or like device.

One problem in the manufacture of drug coated and/or drug eluting stents is the delicacy of the drugs. Many drugs used with stents degrade or lose biological activity when exposed to high temperatures. This has limited the number and type of drugs available for treatment of conditions such as inflammation and restenosis. One approach has been to apply or incorporate the drug at room temperature. Unfortunately, room temperature solutions of drug and polymer fail to adhere to the stent. The drug coming off the stent can migrate to undesirable locations in the body, can create uncertainty in the delivered dosage, and can contaminate personnel handling the stents. The drug can also come off during the manufacturing process.

Additionally, concern over the long-term effects of stents in the body has led to experimentation with bioabsorbable stents, i.e., stents that are absorbed by the body after deployment. Materials used for bioabsorbable stents have included bioabsorbable metals. Unfortunately, the materials used to date have failed to produce satisfactory results. A bioabsorbable stent needs to seal any dissection and provide scaffolding to prevent wall recoil until such scaffolding is no longer needed. A metal bioabsorbable stent such as one made of magnesium lasts a few weeks after deployment in a vessel, but should be present for several months to prevent wall recoil. With the stent gone prematurely, the vessel is reduced in diameter, making the treatment ineffective.

It would be desirable to have a system of and method for stent manufacture that would overcome the above disadvantages.

SUMMARY OF THE INVENTION

One aspect of the present invention provides a method of supercritical stent manufacture including mixing a polymer and a supercritical fluid to form a supercritical mixture; electrically charging a mold to a first polarity, the mold having a mold wall defining a mold plenum; discharging the supercritical mixture through a nozzle; electrically charging the supercritical mixture to a second polarity opposite the first polarity; repeatedly directing the charged supercritical mixture into the mold plenum to form a plurality of polymer layers on the mold wall, the plurality of polymer layers having a predetermined thickness; and separating the plurality of polymer layers from the mold wall.

Another aspect of the present invention provides a system for stent manufacture including means for mixing a polymer and a supercritical fluid to form a supercritical mixture; means for electrically charging a mold to a first polarity, the mold having a mold wall defining a mold plenum; means for discharging the supercritical mixture; means for electrically charging the supercritical mixture to a second polarity opposite the first polarity; means for repeatedly directing the charged supercritical mixture into the mold plenum to form a plurality of polymer layers on the mold wall, the plurality of polymer layers having a predetermined thickness; and means for separating the plurality of polymer layers from the mold wall.

Another aspect of the present invention provides a system for stent manufacture including a mixing chamber operable to mix a polymer and a supercritical fluid to form a supercritical mixture; a nozzle operably connected to the mixing chamber to receive the supercritical mixture and discharge a supercritical mixture stream; a mold having mold walls defining a mold plenum, the mold being operable to receive the supercritical mixture stream in the mold plenum; and a voltage supply operably connected to charge the supercritical mixture stream to a first polarity and the mold walls to a second polarity opposite the first polarity.

The foregoing and other features and advantages of the invention will become further apparent from the following detailed description of the presently preferred embodiments, read in conjunction with the accompanying drawings. The detailed description and drawings are merely illustrative of the invention, rather than limiting the scope of the invention being defined by the appended claims and equivalents thereof.

DETAILED DESCRIPTION

Figure 1:
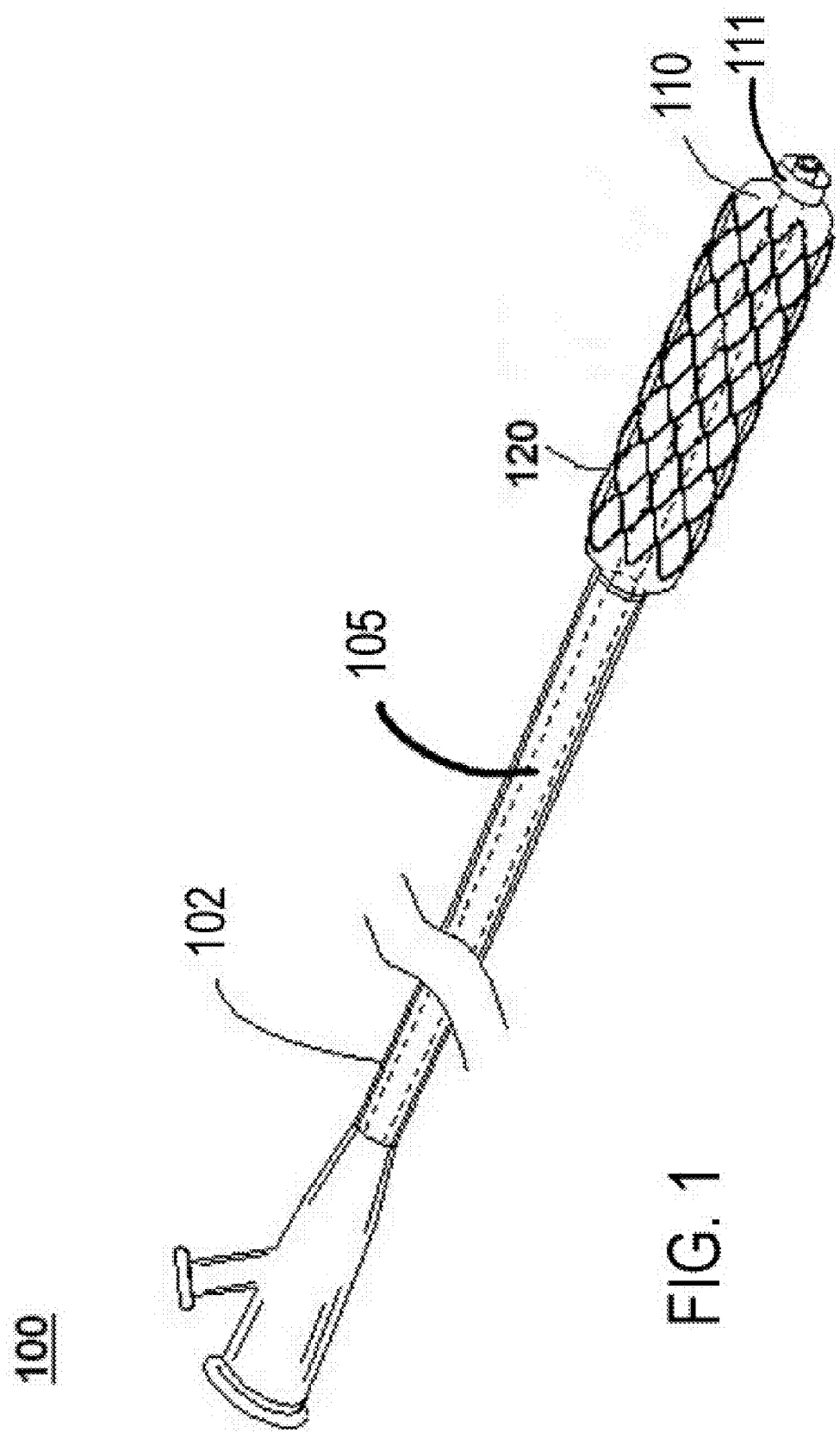
FIG. 1 is a perspective view of a stent delivery system made in accordance with the present invention.

FIG. 1 is a perspective view of a stent delivery system made in accordance with the present invention. The stent delivery system 100 includes a catheter 105, a balloon 110 operably attached to the catheter 105, and a stent 120 disposed on the balloon 110. The balloon 110, shown in an inflated state, can be any variety of balloons capable of expanding the stent 120. The balloon 110 can be manufactured from a material such as polyethylene, polyethylene terephthalate (PET), nylon, Pebax® polyether-block co-polyamide polymers, or the like. In one embodiment, the stent delivery system 100 can include retention means 111, such as mechanical or adhesive structures, for retaining the stent 120 on the balloon 110 until the stent 120 is deployed. The catheter 105 may be any variety of balloon catheters, such as a PTCA (percutaneous transluminal coronary angioplasty) balloon catheter, capable of supporting a balloon during angioplasty. The stent delivery system 100 can also include a sheath 102 through which the stent 120 is delivered to the deployment site.

Figure 2:
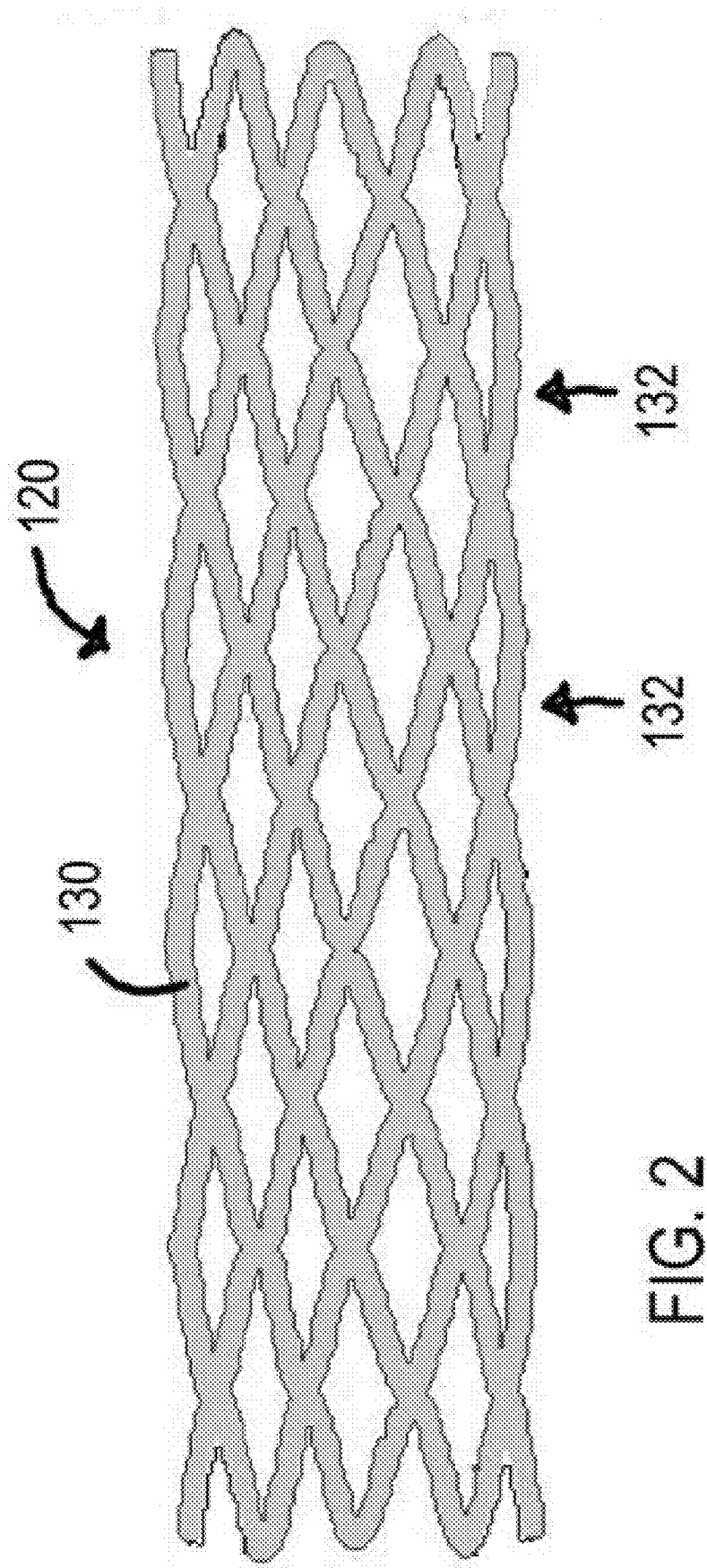
FIG. 2 is a side view of a stent made in accordance with the present invention.

FIG. 2 is a side view of a stent made in accordance with the present invention. The stent 120 includes a stent body 130 with a number of stent body segments 132 made of stent segments 131. The pattern of the stent body segments 132 can be W-shaped or can be a more complex shape with the elements of one segment continuing into the adjacent segment. The stent 120 can be installed in the stent delivery system of FIG. 1 for implantation in a body lumen.

Referring to FIG. 2, the stent body 130 is conventional to stents generally and can be made of a wide variety of medical implantable materials. In one embodiment, the stent body 130 is bioabsorbable. Depending on the material, the stent can be self-expanding, or be expanded by a balloon or some other device. In one embodiment, the stent body 130 can carry a coating, such as a polymer coating carrying one or more therapeutic agents, such as anti-inflammatory agents or anti-proliferative agents. In another embodiment, the stent body 130 can include one or more therapeutic agents within the stent material.

Figure 3:
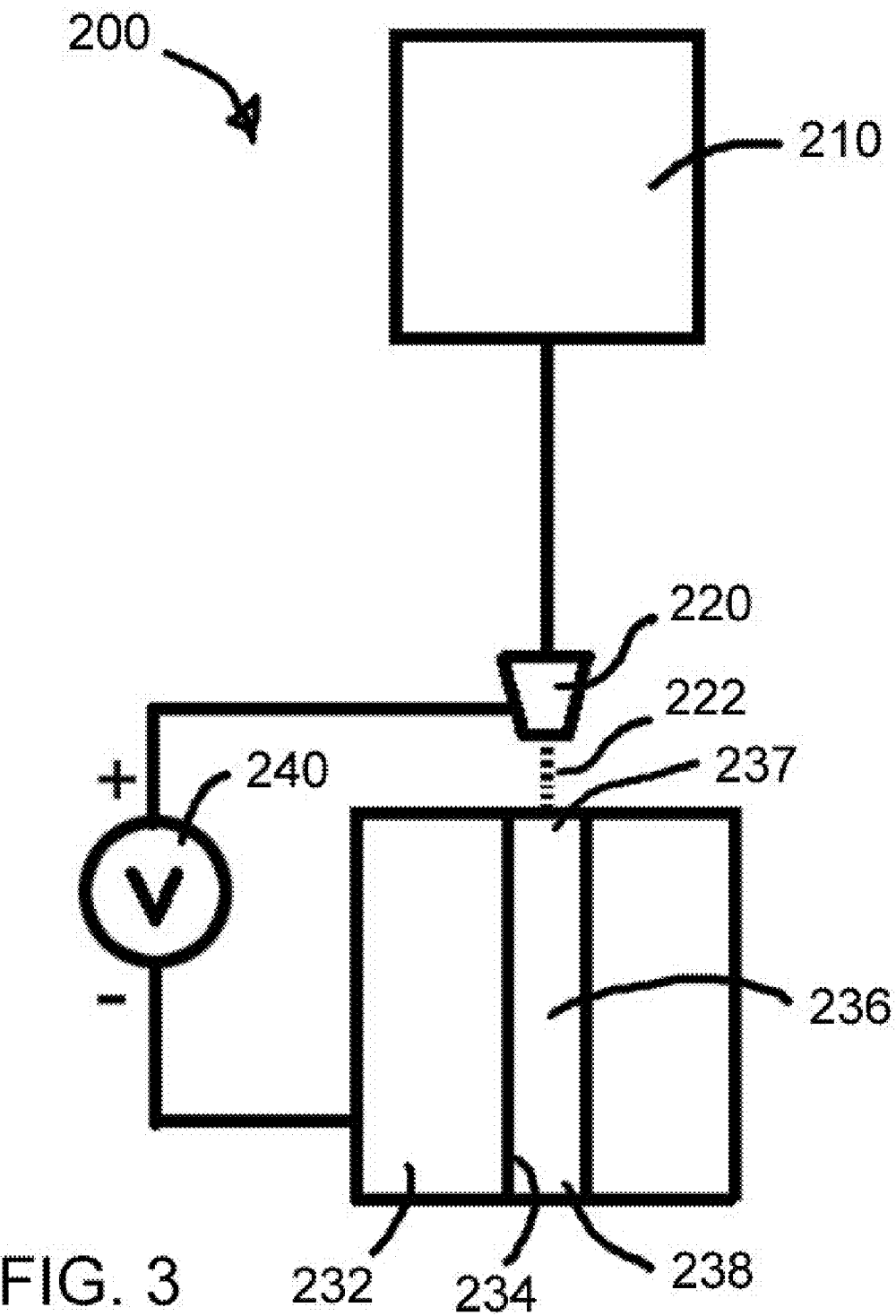
FIG. 3 is a schematic diagram of a system for supercritical stent manufacture in accordance with the present invention.

FIG. 3 is a schematic diagram of a system for supercritical stent manufacture in accordance with the present invention. The system passes a supercritical mixture through a mold, building up polymer layers on the mold wall to form a stent.

The system 200 includes a mixing chamber 210, a nozzle 220, a mold 230, and a voltage supply 240. The mixing chamber 210 mixes a polymer and a supercritical fluid to form a supercritical mixture. In one embodiment, the supercritical mixture also includes a therapeutic agent. In one embodiment, the supercritical mixture is supercritical at a safe temperature for the therapeutic agent. The mixing chamber 210 is operably connected to the nozzle 220 which discharges the supercritical mixture into the mold 230 through the mold inlet 237. The supercritical mixture enters a mold plenum 236 defined by the mold wall 234 of the mold body 232. The voltage supply 240 charges the supercritical mixture stream 222 and the mold 230 to opposite polarities, so the polymers and/or drugs in the supercritical mixture separate from the expanding supercritical fluid and are deposited on the mold wall 234. The supercritical fluid with any residual polymer and/or drug exits the mold 230 through the mold discharge 238. A number of layers of polymers and/or drugs build up on the mold wall 234 to a predetermined thickness, and then the layers can be separated from the mold wall 234. In one embodiment, the layers form a stent blank and additional finishing of the stent blank, such as cutting, shaping, machining, and coating can be performed to form the stent from the stent blank. Those skilled in the art will appreciate that additional flow guides can be used to direct the supercritical mixture into and out of the mold 230.

The charging of the supercritical mixture by the voltage supply 240 can be performed directly through electrical connection to the nozzle 220 or downstream of the nozzle 220 through use of an electrode or screen disposed in the supercritical mixture stream 222. The mold 230 is made of a conductive material, such as a metal, ceramic, polymer, or combinations thereof.

The mixing chamber 210 mixes a supercritical fluid a polymer and/or therapeutic agent to form a supercritical mixture. Exemplary supercritical fluids include carbon dioxide, water, methane, ethane, propane, ethylene, propylene, methanol, ethanol, and acetone. Exemplary polymers include fluoropolymer, polybutylmethacrylate, polyethylene-co-vinyl acetate, styrene isoprene butadiene block copolymers (SIBS), and polylactic acid. In one embodiment, the polymers are biodegradable polymers. Exemplary therapeutic agents include anti-proliferative agents including, but not limited to, macrolide antibiotics including FKBP 12 binding compounds, agents that affect microtubules, estrogens, chaperone inhibitors, protease inhibitors, protein-tyrosine kinase inhibitors, leptomycin B, peroxisome proliferator-activated receptor gamma ligands (PPARγ), hypothemycin, nitric oxide, bisphosphonates, epidermal growth factor inhibitors, antibodies, proteasome inhibitors, antibiotics, anti-inflammatories, anti-sense nucleotides, and transforming nucleic acids. Bioactive agents can also include cytostatic compounds, chemotherapeutic agents, analgesics, statins, nucleic acids, polypeptides and growth factors. Exemplary FKBP 12 binding compounds include sirolimus (rapamycin), tacrolimus (FK506), everolimus (certican or RAD-001), temsirolimus (CCI-779 or amorphous rapamycin 42-ester with 3-hydroxy-2-(hydroxymethyl)-2-methylpropionic acid) and zotarolimus (ABT-578). In one embodiment, the polymer layers including therapeutic agents are sintered at a safe temperature for the therapeutic agent, which is defined herein as a temperature below which the therapeutic agent does not lose efficacy.

FIGS. 4A-4F are side and cross section views of molds for a system for supercritical stent manufacture in accordance with the present invention. The mold has a mold wall defining a mold plenum. Materials, such as polymer and/or therapeutic agents, in the supercritical mixture in the mold plenum form layers on the charged mold wall. The mold is made of a conductive material, such as a metal, ceramic, polymer, or combinations thereof, so that the mold wall can be electrically charged. Once a predetermined thickness of layers form on the mold wall, the layers can be separated from the mold wall and used as a stent or a stent blank. The stent wall can include a pattern to form layers including a pattern as desired for a particular application.

Figure 4E:
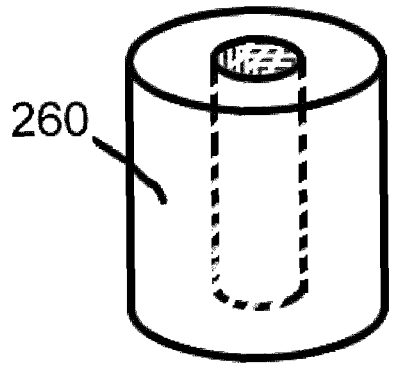
FIGS. 4A-4F are side and cross section views of molds for a system for supercritical stent manufacture in accordance with the present invention.
Figure 4F:
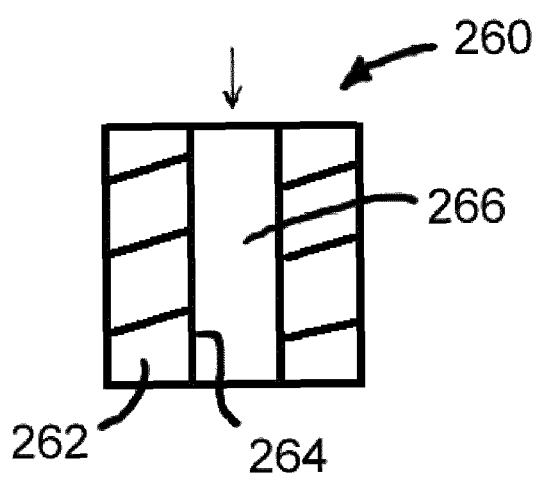
Figure 4C:
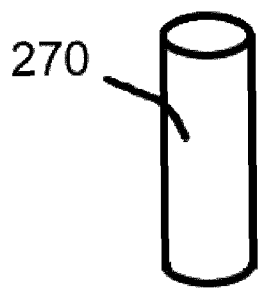
Figure 4D:
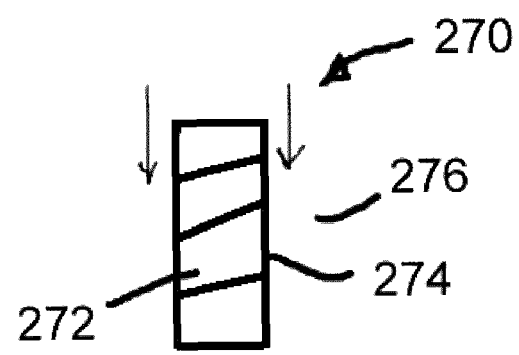
Figure 4A:
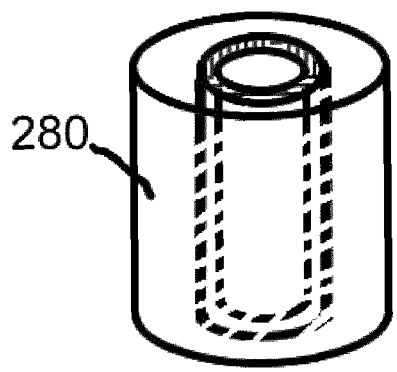
Figure 4B:
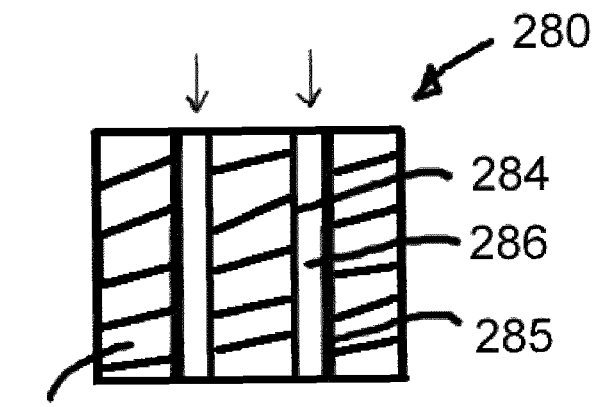

FIGS. 4A & 4B are side and cross section views of an inner diameter mold. The inner diameter mold 260 has a mold body 262 with a mold wall 264 defining a mold plenum 266. The supercritical mixture passes through the mold plenum 266 as indicated by the arrow.

FIGS. 4C & 4D are side and cross section views of an outer diameter mold. The outer diameter mold 270 has a mold body 272 with a mold wall 274 defining a mold plenum 276. In this embodiment, the mold plenum 276 is defined as the space around the mold wall 274. The supercritical mixture passes around the mold wall 274 as indicated by the arrows.

FIGS. 4E & 4F are side and cross section views of an annular mold. The annular mold 280 has a mold body 282 with an inner mold wall 284 and an outer mold wall 285 defining a mold plenum 286. The supercritical mixture passes through the mold plenum 286 as indicated by the arrows. In this embodiment, the mold plenum 286 is an annulus and the layers can form on both the inner mold wall 284 and outer mold wall 285.

When the polymer is a flexible material, the layers can be separated from the mold wall by flexing the layers. Alternatively, the mold can change to free the layers. In one embodiment, the mold is made of a soluble material and the mold is dissolved sufficiently to free the stent. In another embodiment, the mold plenum diameter changes mechanically to free the stent. In yet another embodiment, the mold plenum diameter changes with temperature or electrical charge to free the stent.

Figure 5:
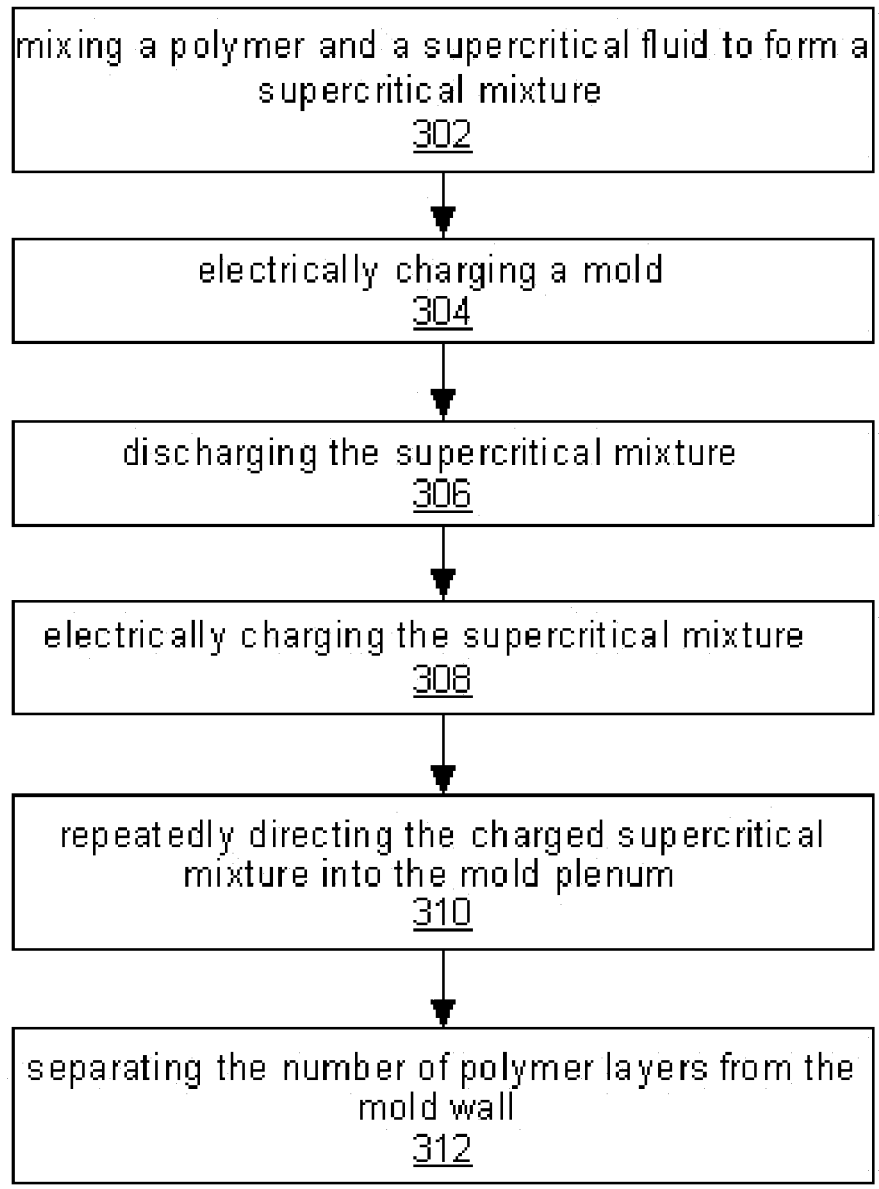
FIG. 5 is a flow chart of a method of supercritical stent manufacture in accordance with the present invention.

FIG. 5 is a flow chart of a method of supercritical stent manufacture in accordance with the present invention. The method 300 includes mixing a polymer and a supercritical fluid to form a supercritical mixture 302; electrically charging a mold 304 to a first polarity, the mold having a mold wall defining a mold plenum; discharging the supercritical mixture 306 through a nozzle; electrically charging the supercritical mixture 308 to a second polarity opposite the first polarity; repeatedly directing the charged supercritical mixture into the mold plenum 310 to form a number of polymer layers on the mold wall, the number of polymer layers having a predetermined thickness; and separating the number of polymer layers from the mold wall 312. The mold can be an outer diameter mold, an inner diameter mold, and an annular mold.

The method 300 can further include sintering the number of polymer layers; finishing the number of polymer layers; and/or applying a therapeutic agent to the mold wall before the repeatedly directing the charged supercritical mixture into the mold plenum.

Mixing a polymer and a supercritical fluid to form a supercritical mixture 302 can include mixing a therapeutic agent into the supercritical mixture and the number of polymer layers include the therapeutic agent. The therapeutic agent can be anti-proliferative agents including, but not limited to, macrolide antibiotics including FKBP 12 binding compounds or agents that affect microtubules, estrogens, chaperone inhibitors, protease inhibitors, protein-tyrosine kinase inhibitors, leptomycin B, peroxisome proliferator-activated receptor gamma ligands (PPARγ), hypothemycin, nitric oxide, bisphosphonates, epidermal growth factor inhibitors, antibodies, proteasome inhibitors, antibiotics, anti-inflammatories, anti-sense nucleotides, and transforming nucleic acids. Bioactive agents can also include cytostatic compounds, chemotherapeutic agents, analgesics, statins, nucleic acids, polypeptides and growth factors, or the like. The method 300 can further include sintering the number of polymer layers including the therapeutic agent. The sintering of the number of polymer layers can be performed at a safe temperature for the therapeutic agent.

Repeatedly directing the charged supercritical mixture into the mold plenum 310 to form a number of polymer layers on the mold wall can include applying a therapeutic agent between adjacent polymer layers. The application of the therapeutic agent can be made using a supercritical mixture application or fluidized coating application. The supercritical mixture application can include mixing a therapeutic agent and a second supercritical fluid to form a second supercritical mixture; discharging the second supercritical mixture through the nozzle; electrically charging the second supercritical mixture to the second polarity opposite the first polarity; and directing the charged second supercritical mixture into the mold plenum to form a therapeutic agent layer on one of the number of polymer layers. The fluidized coating application can include placing an adhesive layer on one of the number of polymer layers; fluidizing a therapeutic agent; and directing the fluidized therapeutic agent onto the adhesive.

It is important to note that FIGS. 1-5 illustrate specific applications and embodiments of the present invention, and are not intended to limit the scope of the present disclosure or claims to that which is presented therein. Upon reading the specification and reviewing the drawings hereof, it will become immediately obvious to those skilled in the art that myriad other embodiments of the present invention are possible, and that such embodiments are contemplated and fall within the scope of the presently claimed invention.

While the embodiments of the invention disclosed herein are presently considered to be preferred, various changes and modifications can be made without departing from the spirit and scope of the invention. The scope of the invention is indicated in the appended claims, and all changes that come within the meaning and range of equivalents are intended to be embraced therein.

The invention claimed is:

1. A method of supercritical stent manufacture comprising:
   mixing a polymer and a supercritical fluid to form a supercritical mixture;
   electrically charging a mold to a first polarity, the mold having a mold wall defining a mold plenum;
   discharging the supercritical mixture through a nozzle;
   electrically charging the supercritical mixture to a second polarity opposite the first polarity;
   repeatedly directing the charged supercritical mixture into the mold plenum to form a plurality of polymer layers on the mold wall, the plurality of polymer layers having a predetermined thickness; and
   separating the plurality of polymer layers from the mold wall.

2. The method of claim 1 further comprising sintering the plurality of polymer layers.

3. The method of claim 1 further comprising finishing the plurality of polymer layers.

4. The method of claim 1 wherein the mixing further comprises mixing a therapeutic agent into the supercritical mixture and the plurality of polymer layers includes the therapeutic agent.

5. The method of claim 4 wherein the therapeutic agent is selected from the group consisting of anti-proliferative agents, macrolide antibiotics, FKBP 12 binding compounds, microtubule effecting agents, estrogens, chaperone inhibitors, protease inhibitors, protein-tyrosine kinase inhibitors, leptomycin B, peroxisome proliferator-activated receptor gamma ligands (PPARγ), hypothemycin, nitric oxide, bisphosphonates, epidermal growth factor inhibitors, antibodies, proteasome inhibitors, antibiotics, anti-inflammatories, anti-sense nucleotides, and transforming nucleic acids, cytostatic compounds, chemotherapeutic agents, analgesics, statins, nucleic acids, polypeptides and growth factors.

6. The method of claim 4 wherein the supercritical mixture is supercritical at a safe temperature for the therapeutic agent.

7. The method of claim 4 further comprising sintering the plurality of polymer layers.

8. The method of claim 7 wherein the sintering comprises sintering the plurality of polymer layers at a safe temperature for the therapeutic agent.

9. The method of claim 1 further comprising applying a therapeutic agent to the mold wall before the repeatedly directing the charged supercritical mixture into the mold plenum.

10. The method of claim 1 wherein the repeatedly directing the charged supercritical mixture into the mold plenum to form a plurality of polymer layers on the mold wall further comprises applying a therapeutic agent between adjacent polymer layers.

11. The method of claim 10 wherein the applying comprises:

mixing a therapeutic agent and a second supercritical fluid to form a second supercritical mixture;

discharging the second supercritical mixture through the nozzle;

electrically charging the second supercritical mixture to the second polarity opposite the first polarity; and directing the charged second supercritical mixture into the mold plenum to form a therapeutic agent layer on one of the plurality of polymer layers.

12. The method of claim 10 wherein the applying comprises:

placing an adhesive layer on one of the plurality of polymer layers;

fluidizing a therapeutic agent; and directing the fluidized therapeutic agent onto the adhesive.

13. The method of claim 1 wherein the mold is selected from the group consisting of an outer diameter mold, an inner diameter mold, and an annular mold.

14. The method of claim 1 wherein the separating comprises separating the plurality of polymer layers from the mold wall by a method selected from the group consisting of dissolving the mold and mechanically changing a mold plenum diameter.

15. The method of claim 1 wherein the polymer is selected from the group consisting of fluoropolymer, polybutylmethacrylate, polyethylene-co-vinyl acetate, styrene isoprene butadiene block copolymers (SIBS), and polylactic acid.

16. The method of claim 1 wherein the polymer is bioabsorbable.

17. The method of claim 1 wherein the supercritical fluid is selected from the group consisting of carbon dioxide, water, methane, ethane, propane, ethylene, propylene, methanol, ethanol, and acetone.

* * * * *